United States Patent
Galluppi et al.

(10) Patent No.: US 9,174,012 B2
(45) Date of Patent: Nov. 3, 2015

(54) DRUG PRODUCTS, DRY POWDER INHALERS AND POLYFLUX COLLIDER ARRANGEMENTS

(75) Inventors: Michael Galluppi, Middlesex, NJ (US); Scott Brown, Princeton, NJ (US); Peter A. Basile, Bloomsbury, NJ (US)

(73) Assignee: MERCK SHARP & DOHME CORP., Rahway, NJ (US)

( * ) Notice: Subject to any disclaimer, the term of this patent is extended or adjusted under 35 U.S.C. 154(b) by 751 days.

(21) Appl. No.: 13/509,700

(22) PCT Filed: Nov. 9, 2010

(86) PCT No.: PCT/US2010/055957
§ 371 (c)(1),
(2), (4) Date: Aug. 9, 2012

(87) PCT Pub. No.: WO2011/059953
PCT Pub. Date: May 19, 2011

(65) Prior Publication Data
US 2013/0000639 A1  Jan. 3, 2013

Related U.S. Application Data

(60) Provisional application No. 61/261,122, filed on Nov. 13, 2009.

(51) Int. Cl.
*A61M 11/00* (2006.01)
*A61M 15/00* (2006.01)

(52) U.S. Cl.
CPC ......... *A61M 15/0065* (2013.01); *A61M 11/002* (2014.02); *A61M 15/0003* (2014.02); *A61M 15/0008* (2014.02); *A61M 2202/064* (2013.01); *A61M 2206/16* (2013.01)

(58) Field of Classification Search
CPC .................. A61M 2202/064; A61M 15/0028; A61M 15/0045; A61M 15/0091; A61M 2206/16; A61M 15/0086
USPC ..................................................... 128/203.15
See application file for complete search history.

(56) References Cited

U.S. PATENT DOCUMENTS

| | | | |
|---|---|---|---|
| 5,429,122 A * | 7/1995 | Zanen et al. | 128/203.15 |
| 5,687,710 A * | 11/1997 | Ambrosio et al. | 128/203.15 |
| 6,273,086 B1 | 8/2001 | Ohki et al. | |
| 6,408,846 B1 | 6/2002 | Ohki et al. | |
| 6,681,768 B2 | 1/2004 | Haaije de Boer et al. | |
| 6,810,872 B1 * | 11/2004 | Ohki et al. | 128/203.15 |
| 7,861,712 B2 * | 1/2011 | Jones et al. | 128/203.15 |

(Continued)

FOREIGN PATENT DOCUMENTS

| | | |
|---|---|---|
| EP | 2082764 A1 | 7/2009 |
| JP | 2000-217919 | 8/2008 |
| WO | WO9414492 | 7/1994 |

*Primary Examiner* — Steven Douglas
(74) *Attorney, Agent, or Firm* — Matthew A. Leff; John C. Todaro (57) ABSTRACT

This disclosure relates to dry powder inhalers and drug products and, more particularly to polyflux colliders useful for de-agglomerating dry powder in dry powder dispensers. Various embodiments provide drug products, dry powder inhalers and polyflux collider arrangement. With various embodiments of the present invention, a polyflux collider is provided which utilizes colliding streams of dry powder to provide desirable de-agglomerating capability for dry powder dispensers.

9 Claims, 12 Drawing Sheets

(56) References Cited

U.S. PATENT DOCUMENTS

| | | | |
|---|---|---|---|
| 2004/0244794 A1* | 12/2004 | Richards | 128/203.15 |
| 2005/0121023 A1* | 6/2005 | Braithwaite | 128/200.14 |
| 2005/0263151 A1 | 12/2005 | Hochrainer et al. | |
| 2006/0147389 A1 | 7/2006 | Staniforth et al. | |
| 2007/0062525 A1 | 3/2007 | Bonney et al. | |
| 2007/0163574 A1 | 7/2007 | Rohrschneider et al. | |
| 2007/0240714 A1 | 10/2007 | Dunne et al. | |
| 2007/0272763 A1 | 11/2007 | Dunne et al. | |
| 2009/0178676 A1* | 7/2009 | Villax et al. | 128/203.15 |

* cited by examiner

DRUG PRODUCTS, DRY POWDER INHALERS AND POLYFLUX COLLIDER ARRANGEMENTS

FIELD OF THE INVENTION

This invention relates to dry powder inhalers and drug products and, more particularly to polyflux colliders useful for de-agglomerating dry powder in dry powder dispensers.

BACKGROUND

Various devices have been used in order to dispense an inhaled metered dose of active pharmaceutical agents such as, including pressurized aerosol devices, nebulizers, pump inhalators and the like. There is growing demand for powder dispensing devices which can dispense metered doses of powdered medicament. With such devices, the powder is withdrawn by inhalation so there is less need to be concerned with synchronizing release of medication with the exact start of inspiration to insure quality of the product delivery. Additionally, dry powders may be more stable than the liquid compositions that may be found in other inhaler device forms.

The particles containing the APA that leave the DPI are desirably within a particular size range that target a specific area of the lung. If the particles containing the APA are too large, they may not enter the respiratory tract, but instead, will be deposited in the mouth or pharynx and possibly enter the digestive tract. Desirably, the DPI will deliver a consistent fine particle dose (FPD) to the targeted area of the lung.

Current dispensers may have a reservoir that holds the powder in the form of agglomerates that contain an active pharmaceutical agent. As the device is actuated, the reservoir will release a dose of agglomerates that contains the appropriate dose of the APA. After the device is actuated, the consumer inhales to force the agglomerates to be carried through inhaler flow channels and break up into a micronized powder. This micronized powder will desirably deliver a consistent dose of the APA to the targeted lung area of the consumer.

Current designs for dry powder inhalers and deagglomeration techniques are described in U.S. Pat. No. 6,240,918, U.S. Pat. No. 5,829,434, U.S. Pat. No. 5,394,868, U.S. Pat. No. 5,687,710. Swirl nozzles have been used to deagglomerate the dry powder. De-agglomeration can be achieved by introducing changes in direction in flow in a channel such that the powder is forced to strike against various channel wall sections due to the changes in direction.

Current reservoir based dry powder inhalers may not efficiently deliver a dose because the DPI may only be capable of delivering a low fine particle fraction and a low fine particle dose. If the fine particle fraction of the dose is low, then the rest of the dose may undesirably be swallowed and absorbed through the digestive tract. Additionally, the total delivered dose of APA may be limited due to the fact that only a certain total amount of powder may be dispensed from the current DPIs. Thus, it would be desirable to increase the efficiency of current DPI's to deliver a higher fine particle fraction and fine particle dose.

SUMMARY

Several embodiments of the present invention provide a dry powder inhaler that is capable of providing a higher fine particle fraction of an APA and also can provide a higher total amount of drug that can be targeted to the desired area of the lung. With various embodiments of the present invention, a polyflux collider is provided which utilizes colliding streams of dry powder to provide desirable de-agglomerating capability for dry powder dispensers.

Various embodiments of the present invention provide for a polyflux collider arrangement that is useful for de-agglomerating dry powder in a powder dispenser during inhalation of a dose of dry powder, the polyflux collider arrangement including spaced-apart first and second inlet openings, a reference plane passing through the centers of the first and second inlet openings; and, a polyflux collider having a body at least partially encompassing a volume and a single exit opening. The first and second inlet openings and the exit opening are in communication with the encompassed volume. The exit opening is spaced from the reference plane, and the center of the exit opening has a reference axis passing therethrough. The reference axis is perpendicular to the reference plane, and the reference axis is spaced from the centers of the first and second inlet openings. Upon inhalation of a dose, negative pressure is applied to the exit opening which causes a first stream of dry powder to be entrained from the first inlet opening into the encompassed volume and directed towards the exit opening. The negative pressure also causes a second stream of dry powder to be entrained from the second inlet opening into the encompassed volume and directed towards the exit opening. The first and second streams of dry powder collide in the encompassed volume to form a collective stream passing through the exit opening, the collective stream defining the dose of dry powder. Advantageously, with various embodiments of the present invention, a polyflux collider is provided which utilizes colliding streams of dry powder and provides suitable de-agglomerating capability for dry powder dispensers.

Other embodiments of the present invention provide a drug product comprising a dry powder inhaler and a dry powder comprising at least one active pharmaceutical agent, wherein the dry powder inhaler comprises at least two reservoirs capable of storing at least one dose of the at least one active pharmaceutical agent, wherein when the dry powder inhaler is actuated, the at least one dose emitted from the at least two reservoirs collides against each other before exiting the dry powder inhaler.

Additional embodiments of the present invention provide a drug product comprising a dry powder inhaler and a dry powder comprising at least two agglomerates comprising at least one active pharmaceutical agent, wherein the dry powder inhaler comprises at least two reservoirs capable of storing at least one dose of the at least one active pharmaceutical agent, wherein when the dry powder inhaler is actuated, the at least two agglomerates collide against each other before exiting the dry powder inhaler.

The dry powder comprising the at least one APA may be in a form of an agglomerate. The drug product may include a polyflux collider arrangement that utilizes colliding streams of dry powder to provide desirable de-agglomeration of dry powders. The agglomerate may also include a substance such as lactose or another active pharmaceutical agent.

Still further embodiments of the present invention provide for a drug product comprising a dry powder inhaler and a dry powder comprising at least one active pharmaceutical agent comprising mometasone, wherein the dry powder inhaler comprises at least two reservoirs capable of storing at least one dose of the at least one active pharmaceutical agent, wherein when the dry powder inhaler is actuated, a fine particle fraction of at least about 55% is obtained.

These and other features of the invention will be better understood through a study of the following detailed description and accompanying drawings.

DETAILED DESCRIPTION

Various embodiments provide a polyflux collider arrangement useful in de-agglomerating a dry powder in a powder dispenser during inhalation of a dose of dry powder. With various embodiments of the present invention, the polyflux collider utilizes colliding streams of dry powder to deagglomerate agglomerates contained in a DPI. The arrangement of various embodiments of the present invention may be utilized with various powder dispensers, but is particularly well-suited for use with dry powder inhalers (DPI's) and drug products.

Additional embodiments of the present invention provide a drug product comprising a dry powder inhaler and a dry powder comprising at least two agglomerates comprising at least one active pharmaceutical agent, wherein the dry powder inhaler comprises at least two reservoirs capable of storing at least one dose of the at least one active pharmaceutical agent, wherein when the dry powder inhaler is actuated, the at least two agglomerates collide against each other before exiting the dry powder inhaler.

Other embodiments of the present invention provide a drug product comprising a dry powder inhaler and a dry powder comprising at least one active pharmaceutical agent, wherein the dry powder inhaler comprises at least two reservoirs capable of storing at least one dose of the at least one active pharmaceutical agent, wherein when the dry powder inhaler is actuated, the at least one dose emitted from the at least two reservoirs collides against each other before exiting the dry powder inhaler.

The drug product may include a dry powder inhaler that includes a polyflux collider arrangement. A polyflux collider acts to accept streams of dry powder from at least two inhalation channels and then combines the two streams into a collective stream, and allows to discharge the collective stream through the exit opening. The dry powder may be in the form of an agglomerate. The agglomerate may also include a substance such as lactose or another active pharmaceutical agent. Useful at least one APA includes one or more of formoterol, mometasone, budesonide, fluticasone, glycopyrrolate, salmeterol, tiotropium, ipratropium, indacaterol and pharmaceutically acceptable salts thereof.

In various embodiments of the present invention, the drug product is capable of emitting a fine particle fraction of at least about 40% upon actuation, is at least about 45%, is at least about 50%, at least about 55%, at least about 60%, at least about 70%, at least about 75%, at least about 80% or at least about 90%.

FIGS. 1 and 2 show an arrangement of parts useable with a powder dispenser. The arrangement of parts of the dry powder inhaler may include a polyflux collider arrangement. The arrangement of parts of the dry powder inhaler may be similar to the arrangement of parts of the dry powder inhaler as shown in U.S. Pat. No. 6,240,918 filed Feb. 20, 1997, which is incorporated by reference herein.

As shown in FIGS. 1 and 2, a reservoir 10 is provided having two reservoir chambers 12, 14 which are formed separately. The reservoir chambers 12, 14 accommodate the dry powder intended for administration. The reservoir chambers 12, 14 may accommodate the same or different dry powders. In this manner, combination drug therapies may be utilized. In addition, larger doses may be achieved than those achievable by the prior art. The reservoir chambers 12, 14 may accommodate the same or different at least one APAs.

A dose plate 16 is associated with the reservoir 10 having dose metering holes 18, 20 formed therein. The dose metering holes 18, 20 are used to accept dry powder from the reservoir chambers 12, 14 in metered amounts for delivery. Inhalation channels 22, 24 are formed through the reservoir 10 so as to be in selective communication with the dose metering holes 18, 20 to achieve proper dose administration.

A nozzle 26 may be provided in the form of a swirl nozzle. With inhalation applied to the nozzle 26, dry powder is inhaled from the dose plate 16, through the inhalation channels 22, 24 and through the nozzle 26 into the mouth of a user. For comfort of the user, a mouthpiece 28 may be provided to mount at least partially about the nozzle 26. In addition, for manufacturing or assembly reasons, additional components, such as a cup-shaped body 30 may be provided. The body 30 may be formed to accommodate the reservoir 10 therein and provide assembly to surrounding components. Other arrangements and configurations of these components may be used. A configuration of a dose plate, inhalation channel and nozzle (e.g., a swirl nozzle) is disclosed in U.S. Pat. No. 6,240,918.

A polyflux collider 32 is provided having a body 34 which encompasses at least partially an encompassed volume 36. The body 34 may include a disc-shaped top 38 with a downward depending skirt 40 extending therefrom. The encompassed volume 36 is at least partially encompassed by the top 38 and the skirt 40. The polyflux collider 32 is located so as to accept flow from the inhalation channels 22, 24 and direct the flow to the nozzle 26. The polyflux collider 32 includes an exit opening 42 located to direct the exit discharge from the encompassed volume 36. The discharge from the exit opening 42 may be directed into the nozzle 26. The polyflux collider 32 acts to accept streams of dry powder from both of the inhalation channels 22, 24, combine the two streams into a collective stream, and discharge the collective stream through the exit opening 42.

The inhalation channels 22, 24 terminate at first and second inlet openings 44, 46, respectively, which are inlet openings into the polyflux collider 32. The first and second inlet openings 44, 46 may be formed on the body 34 of the polyflux collider 32, but may be also formed on a separate component, such as on the reservoir 10, at the ends of the inhalation channels 22, 24 or at openings 48, 50 formed in a secondary component, such as the body 30. In any regard, the first and second inlet openings 44, 46 are positioned to be in communication with the encompassed volume 36. In addition, the exit opening 42 is in communication with the encompassed volume 36.

Figure 5:
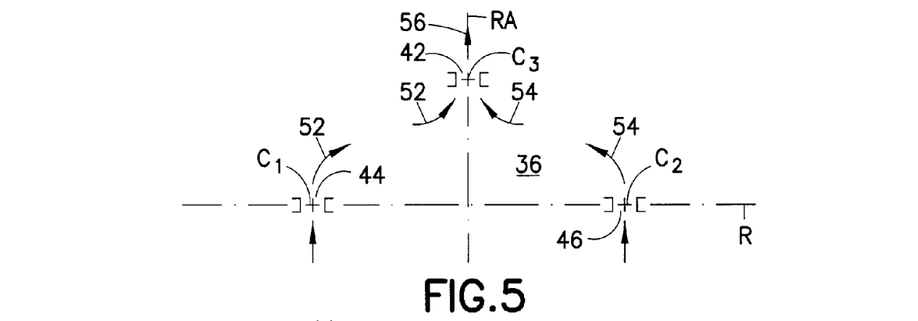
FIG. 5 is a schematic showing flowpaths of streams of dry powder in a polyflux collider arrangement formed in accordance with various embodiments of the present invention.
Figure 6:
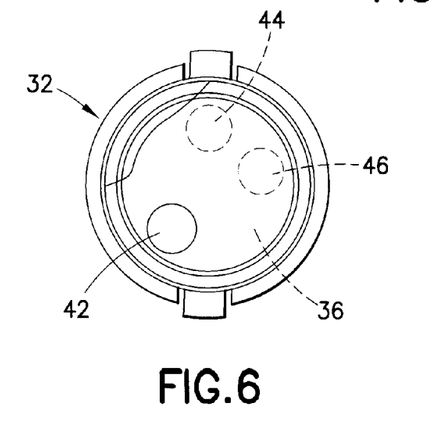
FIGS. 6 and 7 are top and bottom plan views, respectively of a polyflux collider arrangement based on the arrangement of parts shown in FIGS. 10 and 11.
Figure 7:
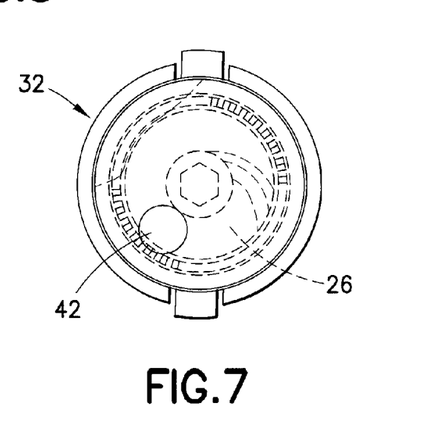
Figure 8:
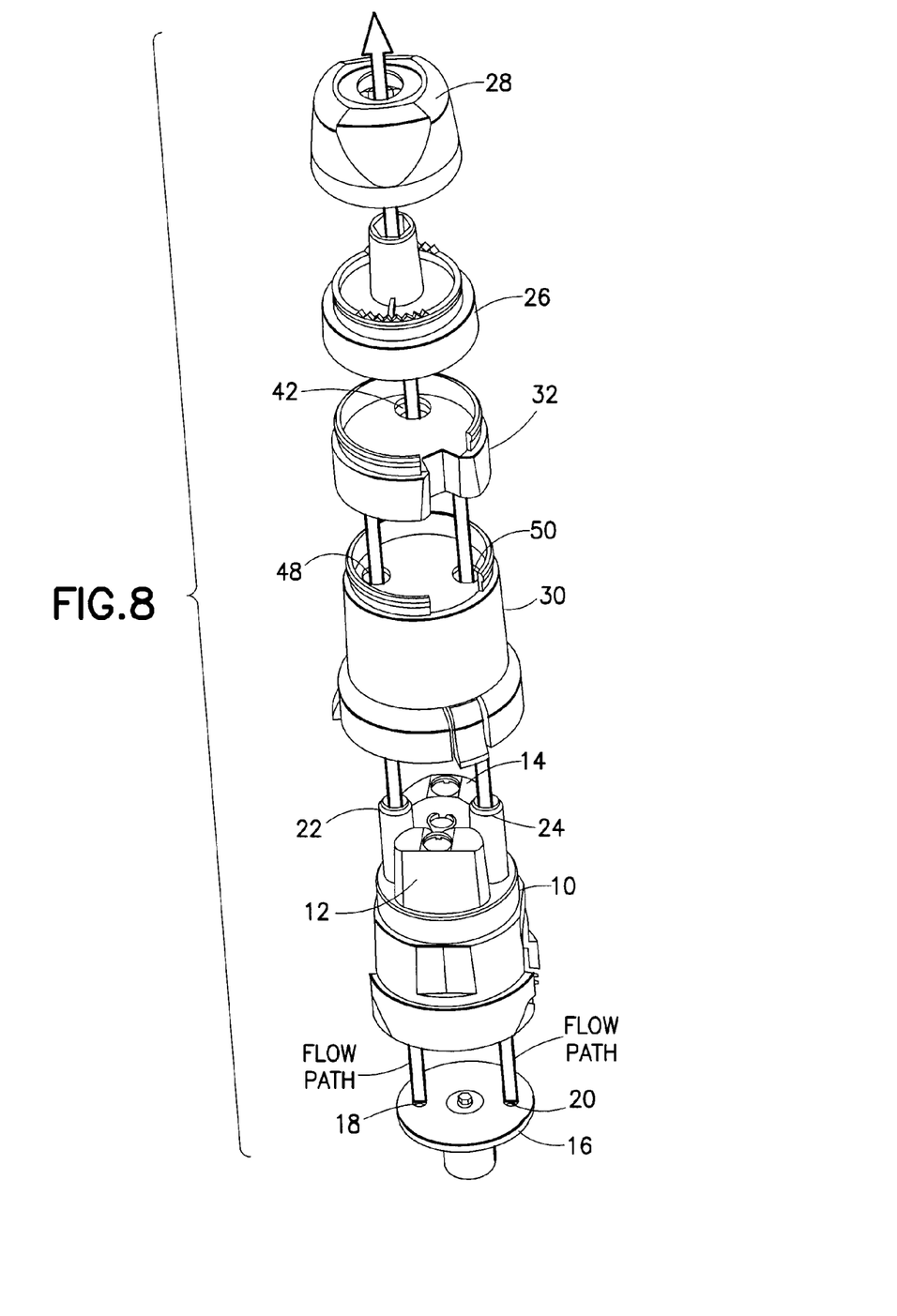
FIGS. 8 and 9 schematically show the flowpath of dry powder through the arrangement of parts of FIGS. 1 and 2.
Figure 9:
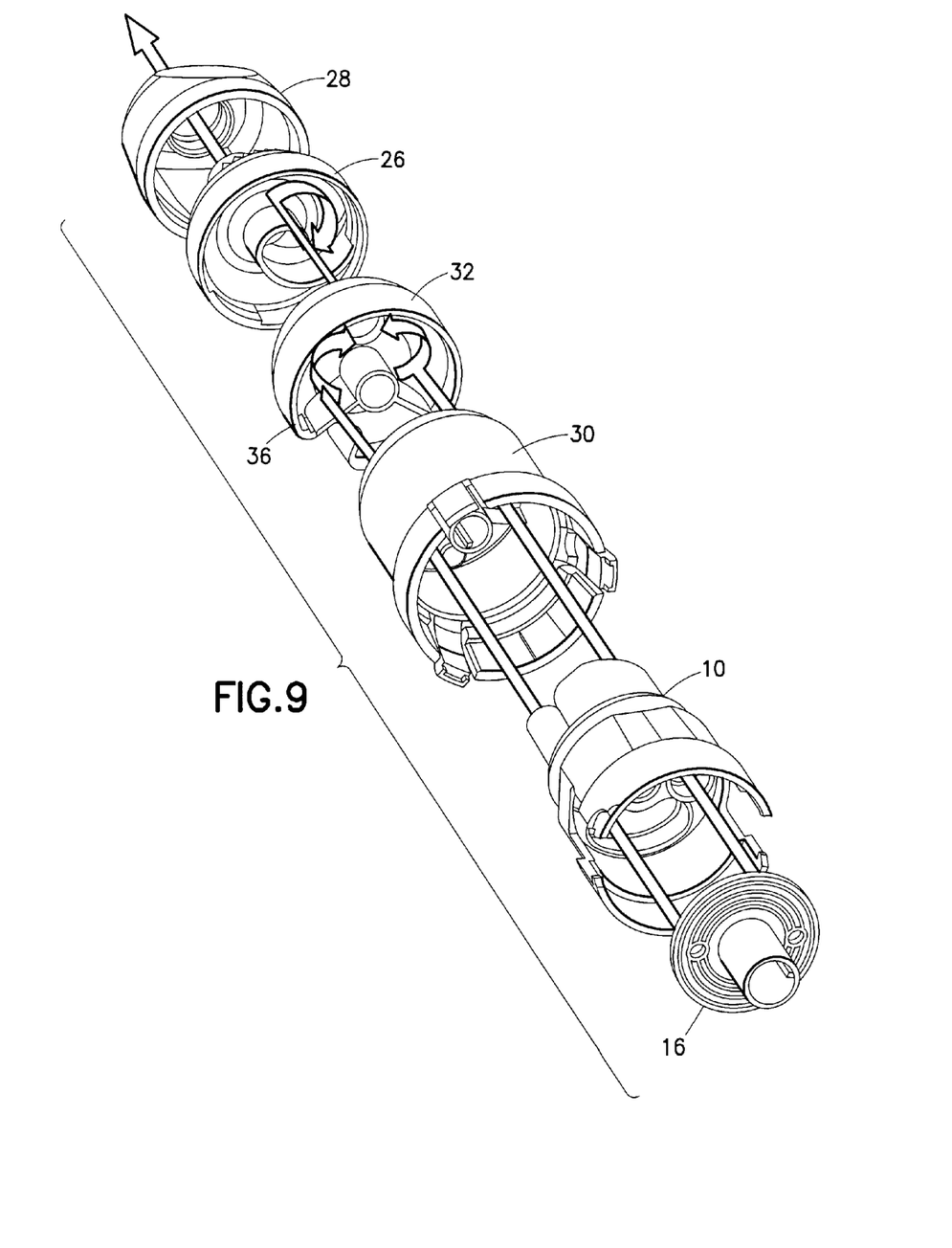
Figure 10:
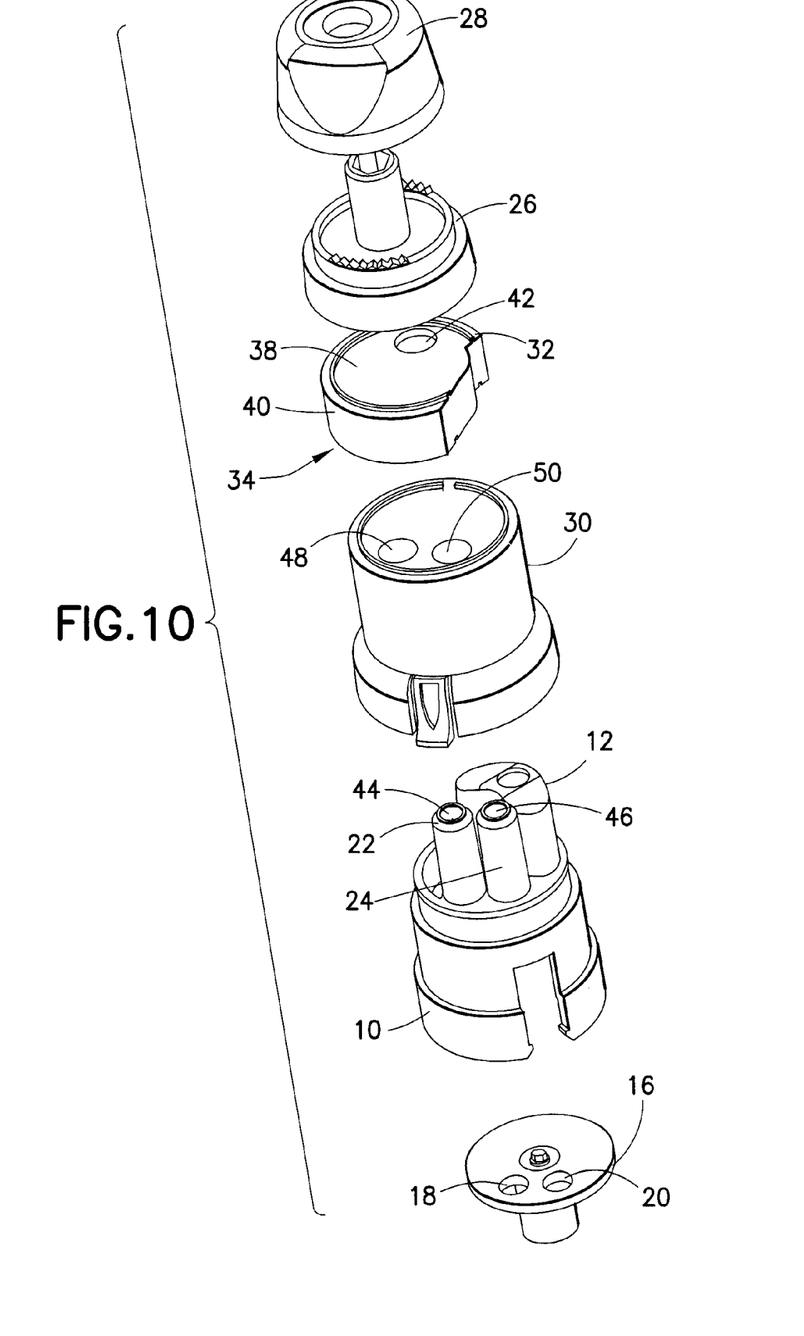
FIGS. 10 and 11 are exploded views of a variation of the arrangement of parts of FIGS. 1 and 2.
Figure 11:
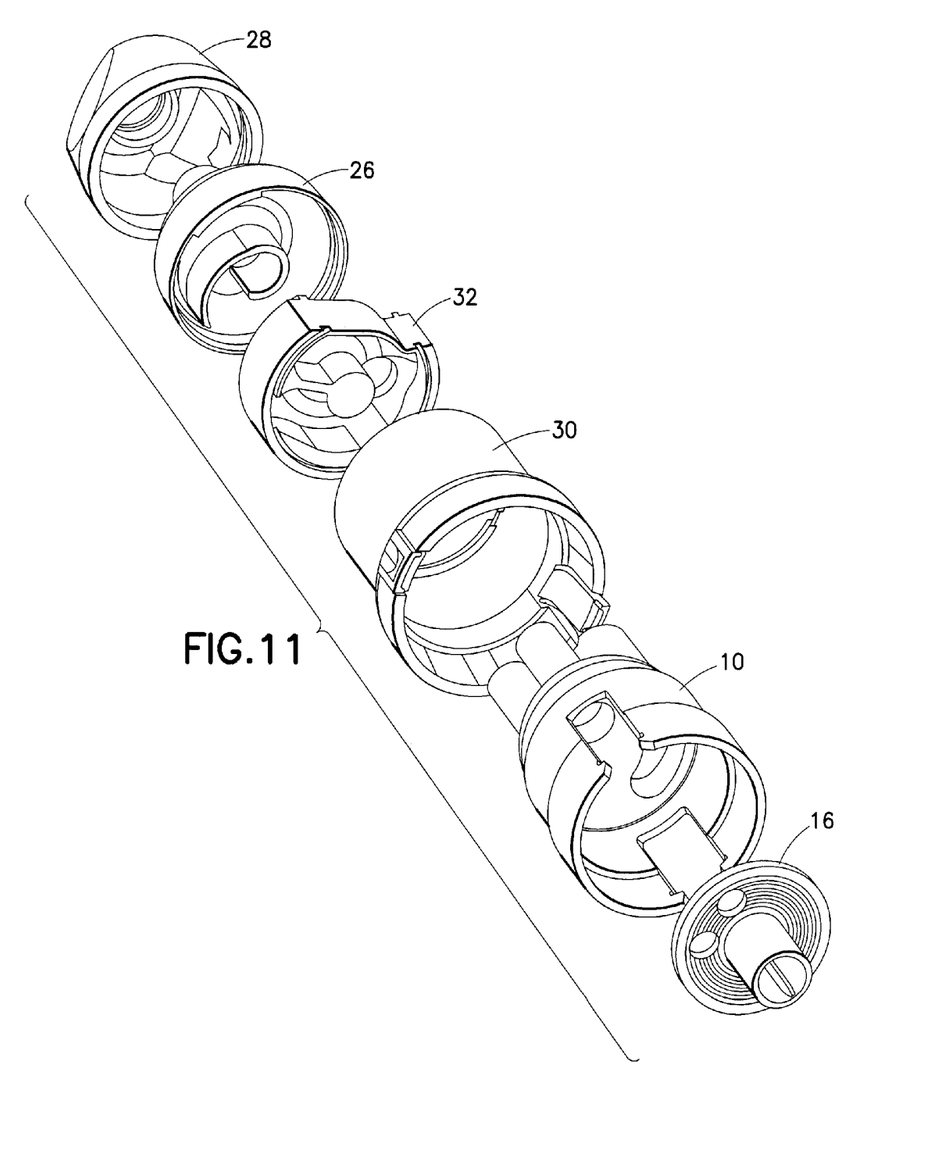
Figure 12:
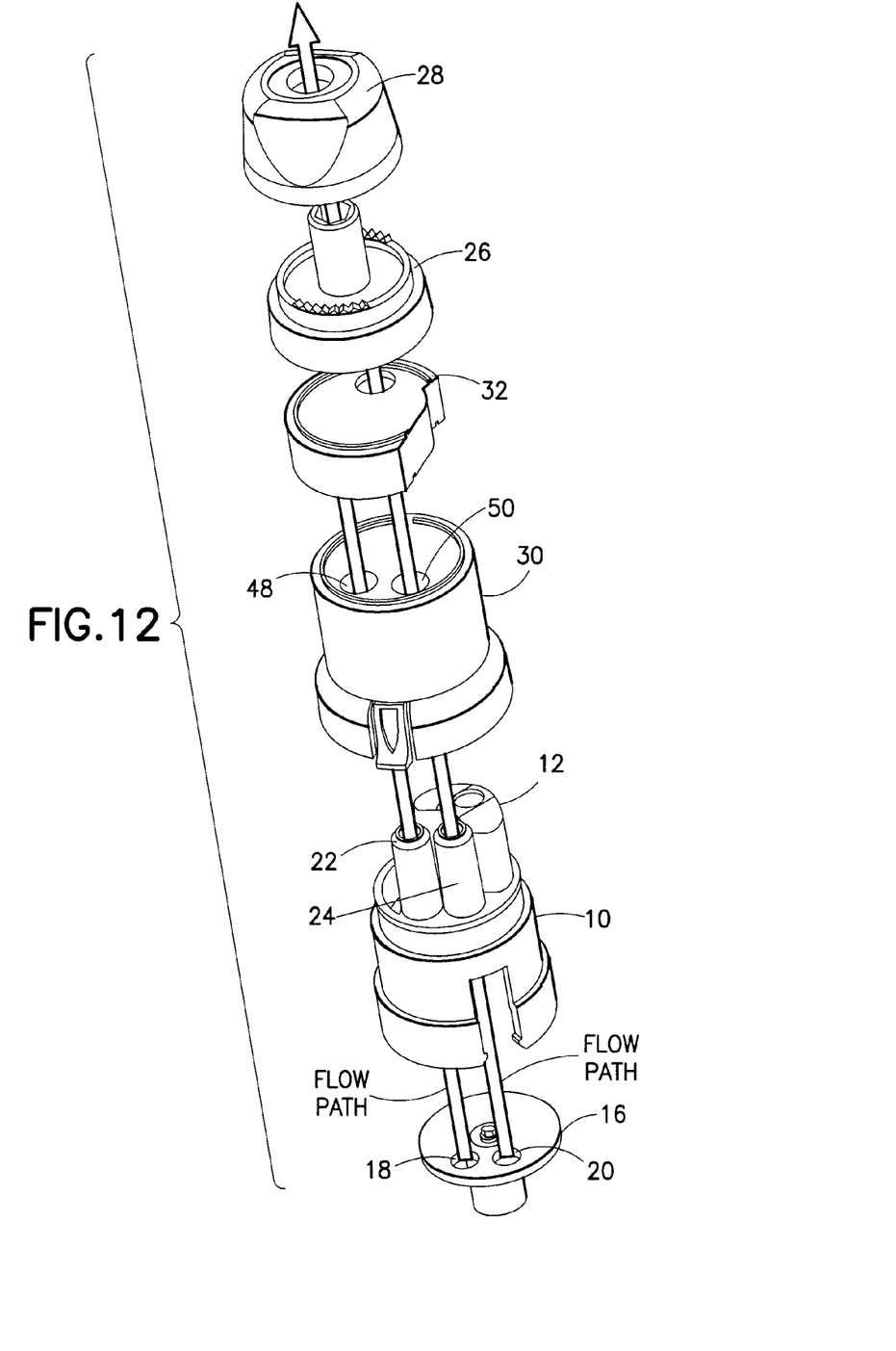
FIGS. 12 and 13 schematically show the flowpath of dry powder through the arrangement of parts of FIGS. 10 and 11.
Figure 13:
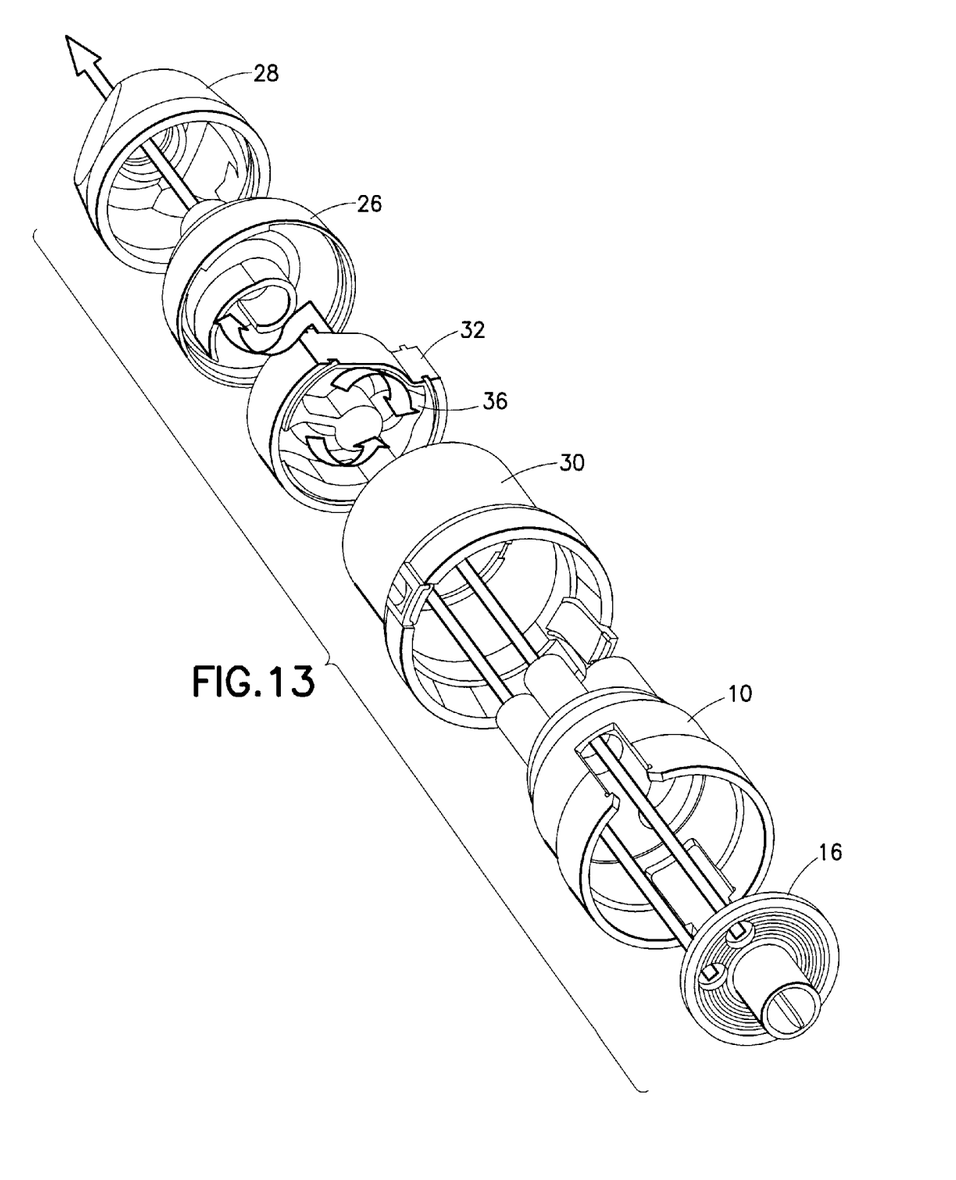
Figure 14:
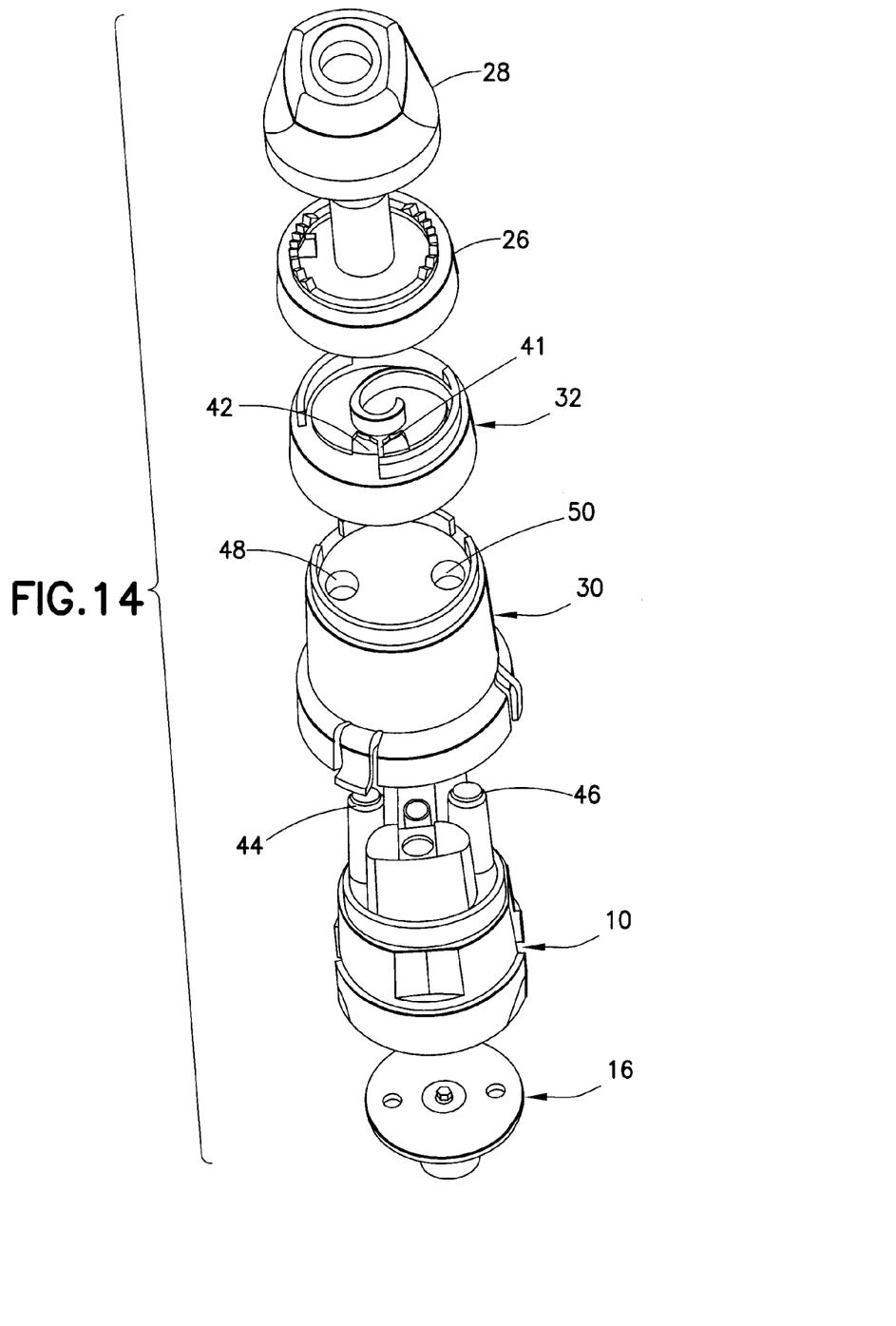
FIGS. 14-15 are exploded views of an arrangement of parts, including a polyflux collider arrangement formed in accordance with various embodiments of the present invention, for use with powder dispensers.
Figure 15:
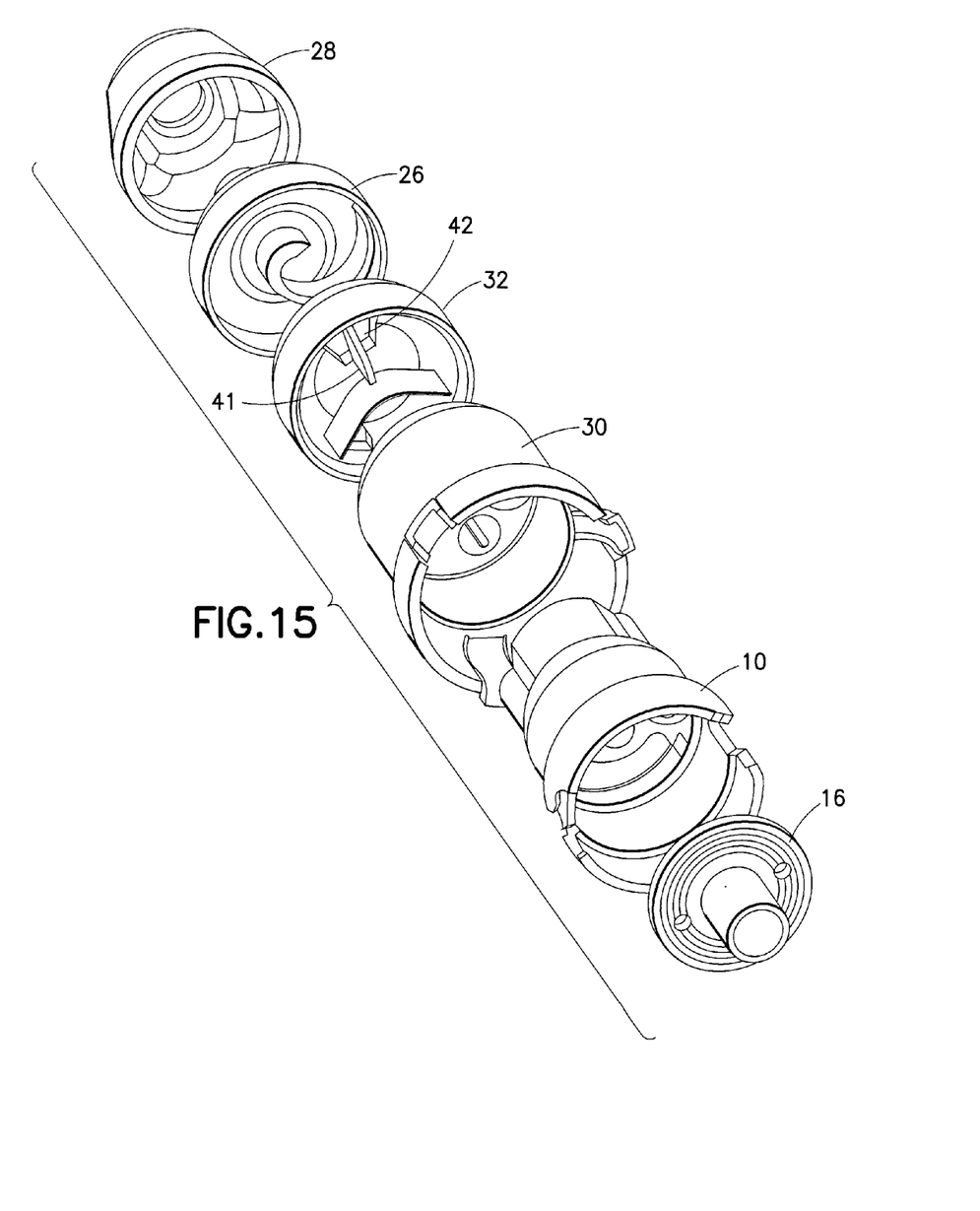

As shown in FIG. 5, a hypothetical reference plane R is positioned to pass through the centers C1, C2 of the first and second inlet openings 44, 46. The exit opening 42 is spaced from the reference plane R. In addition, a hypothetical reference axis RA passes through center C3 of the exit opening 42 with the reference axis RA being perpendicular to the reference plane R. The reference axis RA is spaced from the centers C1, C2 of the first and second inlet openings 44, 46. With this arrangement, flow of dry powder coming through the polyflux collider 32 will experience two transverse changes in direction. A first transverse change of direction will be experienced upon passing into the encompassed volume 36 through the first or second inlet openings 44, 46. A second transverse change of direction will be experienced upon passing from the encompassed volume 36 and through the exit opening 42.

As shown in FIGS. 14-18, another embodiment is exemplified having an arrangement wherein at least one divider 41 spans across at least a portion of, preferably the entirety of, the exit opening 42. The divider 41 may act to guide the flow of dry powder through the exit opening 42. Preferably, the divider 41 is formed as a wall (FIG. 18) extending in a direction parallel to the intended direction of the flow of dry powder (i.e., in a direction parallel to the reference axis RA). It is further preferred that the divider 41 be configured relative to the exit opening 42 so as to divide the exit opening 42 into symmetrical parts, e.g. being centrally located to divide the exit opening 42 into two symmetrical parts or with a plurality of the dividers 41 being utilized spaced apart to divide the exit opening 42 into a plurality of equal parts. This arrangement permits for the divider 41 to divide the flow into generally equal portions while flowing past the divider 41.

Figure 16:
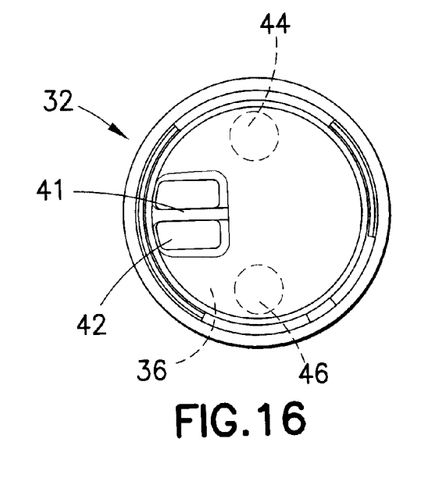
FIGS. 16-17 are top and bottom plan views, respectively, of a polyflux collider arrangement based on the arrangement of parts shown in FIGS. 14 and 15; and, FIG. 18 is a schematic showing flowpaths of streams of dry powder in a polyflux collider arrangement formed in accordance with the embodiment shown in FIGS. 14-17.
Figure 17:
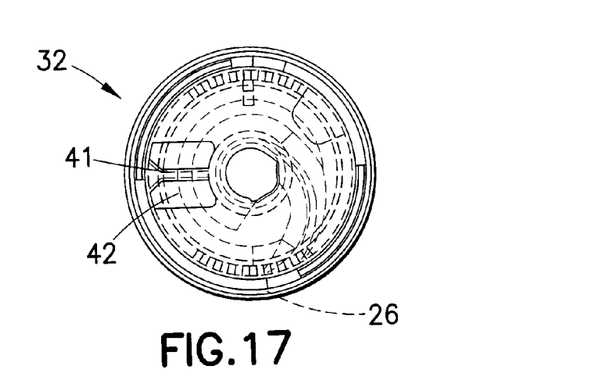

As indicated above, streams of dry powder from both the first and second inlet openings 44, 46 are intended to pass through the single exit opening 42. The exit opening 42 may be sufficiently sized so as to not provide pressure resistance to flow. The exit opening 42 may be at least as great in area as the larger of the first and second inlet openings 44, 46. The exit opening 42 may be formed of various configurations, such as being circular (FIG. 1) or generally rectangular (FIG. 16). The first and second inlet openings 44, 46 may be likewise formed of various configurations.

During use, a user inhales through the nozzle 26 so as to draw a dose of dry powder. With such inhalation, negative pressure is applied to the exit opening 42 which causes a first stream of dry powder 52 to be entrained from the first inlet opening 44 into the encompassed volume 36 and directed towards the exit opening 42. The negative pressure also causes a second stream of dry powder 54 to be entrained through the second inlet opening 46, into the encompassed volume 36 and directed at the exit opening 42. The first and second streams 52, 54 may be configured to be directed at the exit opening 42 from different directions. The first and second streams 52, 54 are caused to collide prior to entry of the exit opening 42. A collective stream 56 is formed of the first and second streams 52, 54 which passes through the exit opening 42. The collective stream 56 is directed into the nozzle 26 and discharged therefrom in administering a dose to a patient.

The collision of the first and second streams 52, 54 causes de-agglomeration of the dry powder contained therein. A portion of the kinetic energy resident in the first and second streams 52, 54 is released upon collision to provide a de-agglomerating effect on colliding particles. With prior art swirl nozzles and other de-agglomerating constructs, powder is caused to collide with surrounding walls and/or structures to obtain de-agglomeration. With colliding streams as obtained with multiple embodiments of the present invention, the release of the kinetic energy not only de-agglomerates the particles releasing the kinetic energy, but, also, the released kinetic energy acts on the colliding particles to impart a de-agglomerating effect thereto. Various embodiments of the present invention provide more efficient utilization of kinetic energy.

An inhaler with the polyflux collider includes two areas where kinetic energy is released during a collision. One of these areas is the traditional impact of the agglomerate stream on the walls of the nozzle. The second and additional area is the region of the polyflux collider.

The polyflux collider may be more efficient than the nozzle section, because the angle between the stream velocity and the wall or apposing stream is zero degrees. In the nozzle area, the flow hits the wall at an angle, therefore the perpendicular component of momentum contributes to the impact and the fraction of the kinetic energy parallel to the nozzle's wall does not necessarily contribute to de-agglomeration.

With the polyflux collider, the two streams meet head on and all of the kinetic energy can participate in de-agglomeration.

Two areas of de-agglomeration include the collider and the nozzle act in sequence. The smaller particles resulting from polyflux collisions move down stream to the nozzle, where they can impact the nozzle walls and experience further de-agglomeration.

Figure 18:
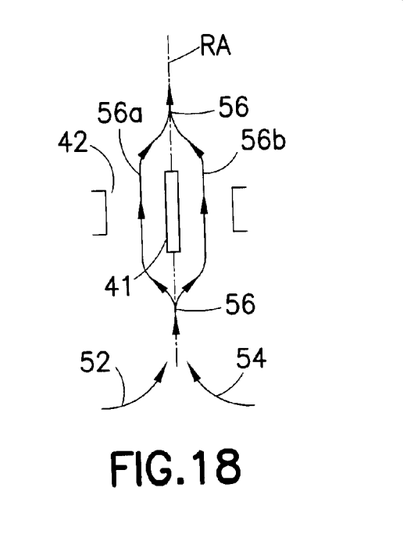

With use of the one or more dividers 41, as shown in FIG. 18, the collective stream 56 is caused to be divided into a plurality of divided streams 56a, 56b while passing through the exit opening 42. The divided streams 56a, 56b re-join downstream of the divider(s) 41 to re-form the collective stream 56, which further proceeds through the nozzle 26 for administration to a patient. Particles in the collective stream 56 may impact against the divider(s) 41 and/or against each other with the divided streams 56a, 56b re-joining to re-form the collective stream 56 downstream of the divider(s) 41. This additional impaction may provide further de-agglomeration.

As shown in FIGS. 1-4, 8 and 9, the reservoir 10 may include separate reservoirs 12, 14. With reference to FIGS. 6, 7 and 10-13, the reservoir 10 may include one reservoir 12 which supplies the two dose metering holes 18, 20. With this arrangement, a single dry powder may be administered but in much larger doses than with respect to the use of a single inhalation channel. The polyflux collider 32 functions in the same manner here as described above.

The polyflux collider 32 may be formed with one or more boundary walls 58 defining a portion of the boundary of the encompassed volume 36. The boundary walls 58 may extend downwardly from the top 38 and radially inwardly from the skirt 40. A center post 60 may be provided to facilitate assembly and/or also to provide a partial boundary of the encompassed volume 36.

More than two inlet openings may be utilized (e.g., more than reservoirs and/or inhalation channels may be utilized). Also, the polyflux collider arrangement may be used in series where streams of dry powder are caused to pass through two or more polyflux colliders with multiple collisions being experienced. In addition, a polyflux collider may be configured to accommodate two or more of the encompassed volumes. The multiple encompassed volumes in a single polyflux collider may be isolated from one another and that each have a single exit opening. As such, a polyflux collider arrangement may be provided which is configured to accept a plurality of streams of dry powder with discharge of a lesser quantity of streams. For example, a polyflux collider may be configured to accept four streams of dry powder and discharge two streams. The two discharge streams may be combined in a second polyflux collider.

The at least one APA may be in the form of an agglomerate. Agglomerates of drug alone or with another substance may be utilized, such as those agglomerates described in U.S. Pat. No. 6,503,537 filed Apr. 2, 2001, which is incorporated herein by reference. Any method of agglomerating the solid binder and the pharmacologically active agent may be used. Useful agglomerating methods include those which can be accomplished without converting the amorphous content of the solid binder to a crystalline form, prematurely, and which does not require the use of additional binder, can be practiced in accordance with the present invention.

Useful agglomerates include agglomerates ranging in size from between about 100 to about 1500 μm. The agglomerates may have an average size of between about 300 and about 1,000 μm. Useful agglomerates may have a bulk density which ranges from between about 0.2 to about 0.4 g/cm$^3$ or between about 0.29 to about 0.38 g/cm$^3$.

It is useful to have a tight particle size distribution. In this context, particle size refers to the size of the agglomerates. Preferably, no more than about 10% of the agglomerates are 50% smaller or 50% larger than the mean or target agglomerate size. For example, for an agglomerate of 300 μm, no more than about 10% of the agglomerates will be smaller than about 150 μm or larger than about 450 μm.

A useful method of preparing the agglomerates is described in U.S. Pat. No. 6,503,537, which is incorporated herein. Suitable methods involve mixing preselected amounts of one or more pharmacologically active agent(s) and the micronized, amorphous content containing, dry solid binder in a ratio of between about 100:1 and about 1:500; between about 100:1 and about 1:300 (drug:binder); between about 20:1 to about 1:20 or a ratio of about 1:3 to about 1:10 relative to the amount of the solid binder.

Useful agglomerates may have a strength which ranges from between about 50 mg and about 5,000 mg and most preferably between about 200 mg and about 1,500 mg. The crush strength was tested on a Seiko TMA/SS 120C Thermomechanical Analyzer available from Seiko Instruments, Inc. Tokyo, Japan, using procedures available from the manufacturer. It should be noted that strength measured in this manner is influenced by the quality and extent of the interparticulate crystalline bonding described herein. However, the size of the agglomerates also plays a role in the measured crush strength. Generally, larger agglomerates require more force to crush than do the smaller particles.

Various pharmaceutical active agents may be utilized. Suitable at least one active pharmaceutical agents include but are not limited to an anticholinergic, a corticosteroid, a long acting beta agonist, short acting beta agonist, a phosphodiesterase IV inhibitor. Suitable medicaments may be useful for the prevention or treatment of a respiratory, inflammatory or obstructive airway disease. Examples of such diseases include asthma or chronic obstructive pulmonary disease.

Suitable anticholinergics include (R)-3-[2-hydroxy-2,2-(dithien-2-yl)acetoxy]-1-1[2-(phenyl)ethyl]-1-azoniabicyclo[2.2.2]octane, glycopyrrolate, ipratropium bromide, oxitropium bromide, atropine methyl nitrate, atropine sulfate, ipratropium, belladonna extract, scopolamine, scopolamine methobromide, methscopolamine, homatropine methobromide, hyoscyamine, isopriopramide, orphenadrine, benzalkonium chloride, tiotropium bromide, GSK202405, an individual isomer of any of the above or a pharmaceutically acceptable salt or hydrate of any of the above, or a combination of two or more of the above.

Suitable corticosteroids includes mometasone furoate; beclomethasone dipropionate; budesonide; fluticasone; dexamethasone; flunisolide; triamcinolone; (22R)-6.alpha.,9.alpha.-difluoro-11.beta., 21-dihydroxy-16.alpha.,17.alpha.-propylmethylenedioxy-4-pregnen-3,20-dione, tipredane, GSK685698, GSK799943 or a pharmaceutically acceptable salt or hydrate of any of the above, or a combination of two or more of the above.

Suitable long acting beta agonist include carmoterol, indacaterol, TA-2005, salmeterol, formoterol, or a pharmaceutically acceptable salt or hydrate of any of the above, or a combination of two or more of the above. Suitable short acting beta agonist include albuterol, terbutaline sulfate, bitolterol mesylate, levalbuterol, metaproterenol sulfate, pirbuterol acetate or a pharmaceutically acceptable salt or hydrate of any of the above, or a combination of two or more of the above.

Suitable phosphodiesterase IV inhibitors include cilomilast, roflumilast, tetomilast, 1-[[5-(1(S)-aminoethyl)-2-[8-methoxy-2-(trifluoromethyl)-5-quinolinyl]-4-oxazolyl]carbonyl]-4(R)-[(cyclopropylcarbonyl)amino]-L-proline, ethyl ester or a pharmaceutically acceptable salt or hydrate of any of the above, or a combination of two or more of the above.

In certain embodiments of the present invention the at least one active pharmaceutical agent includes a corticosteroid, such as mometasone furoate. Mometasone furoate is an anti-inflammatory corticosteroid having the chemical name, 9,21-Dichloro-11(beta), 17-dihydroxy-16(alpha)-methylpregna-1,4-diene-3,20-dione 17-(2 furoate). It is practically insoluble in water; slightly soluble in methanol, ethanol, and isopropanol; soluble in acetone and chloroform; and freely soluble in tetrahydrofuran. Its partition coefficient between octanol and water is greater than 5000. Mometasone can exist in various hydrated, crystalline and enantiomeric forms, e.g., as a monohydrate.

EXAMPLES

Tests were conducted to evaluate the efficacy of the polyflux collider arrangement. All tests utilized mometasone furoate in dry powder form. Also, all tests were conducted on an Andersen design cascade impactor, such as that sold by the Thermo Scientific division of Thermo Fisher Scientific, Inc. of Waltham, Mass. at 60 l/min with a test interval of 2 seconds.

Figure 3:
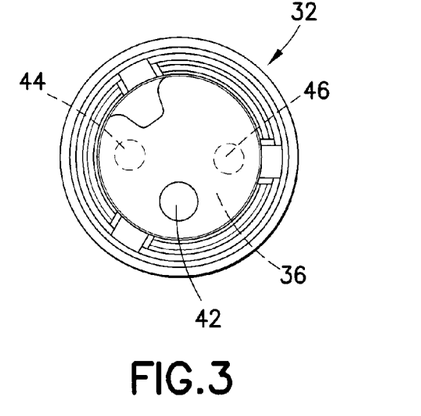
FIGS. 3 and 4 are top and bottom plan views, respectively, of a polyflux collider arrangement based on the arrangement of parts shown in FIGS. 1 and 2.
Figure 4:
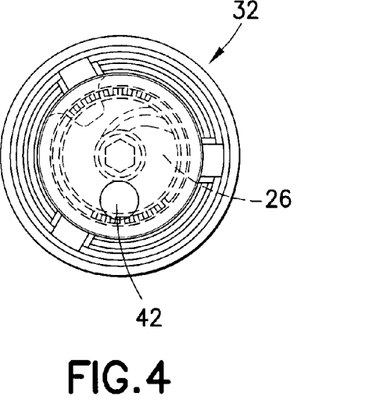

With respect to Table 1, a polyflux collider arrangement, as shown in FIGS. 3 and 4, was tested with a dose containing 400 μg of dry powder of mometasone furoate. The test was conducted with simulated inhalation. It is most desirable to recover a maximum level of dry powder at fine particle size (taken to be equal to or smaller than 6.5 μm).

With the polyflux collider arrangement of FIGS. 3 and 4, a fine particle fraction (% FPF) of approximately 55.8%-60.4% was achievable. This correlates to a fine particle dose (FPD) experienced by a patient of approximately 213-220 μg (out of 400 μg).

TABLE 1

400 μg with Polyflux Collider Arrangement

|  | Dose 1 | Dose 2 | Dose 3 | Average | Standard Deviation |
|---|---|---|---|---|---|
| Total Recovery | 381.74723 | 372.70743 | 365.81824 | 373.42430 | 7.99 |
| % Recovery | 95.43681 | 93.17686 | 91.45456 | 93.35608 | 2.00 |
| % FPF | 55.80391 | 58.98913 | 60.40998 | 58.40101 | 2.36 |
| FPD | 213.02989 | 219.85687 | 220.99072 | 217.95916 | 4.31 |

Figure 1:
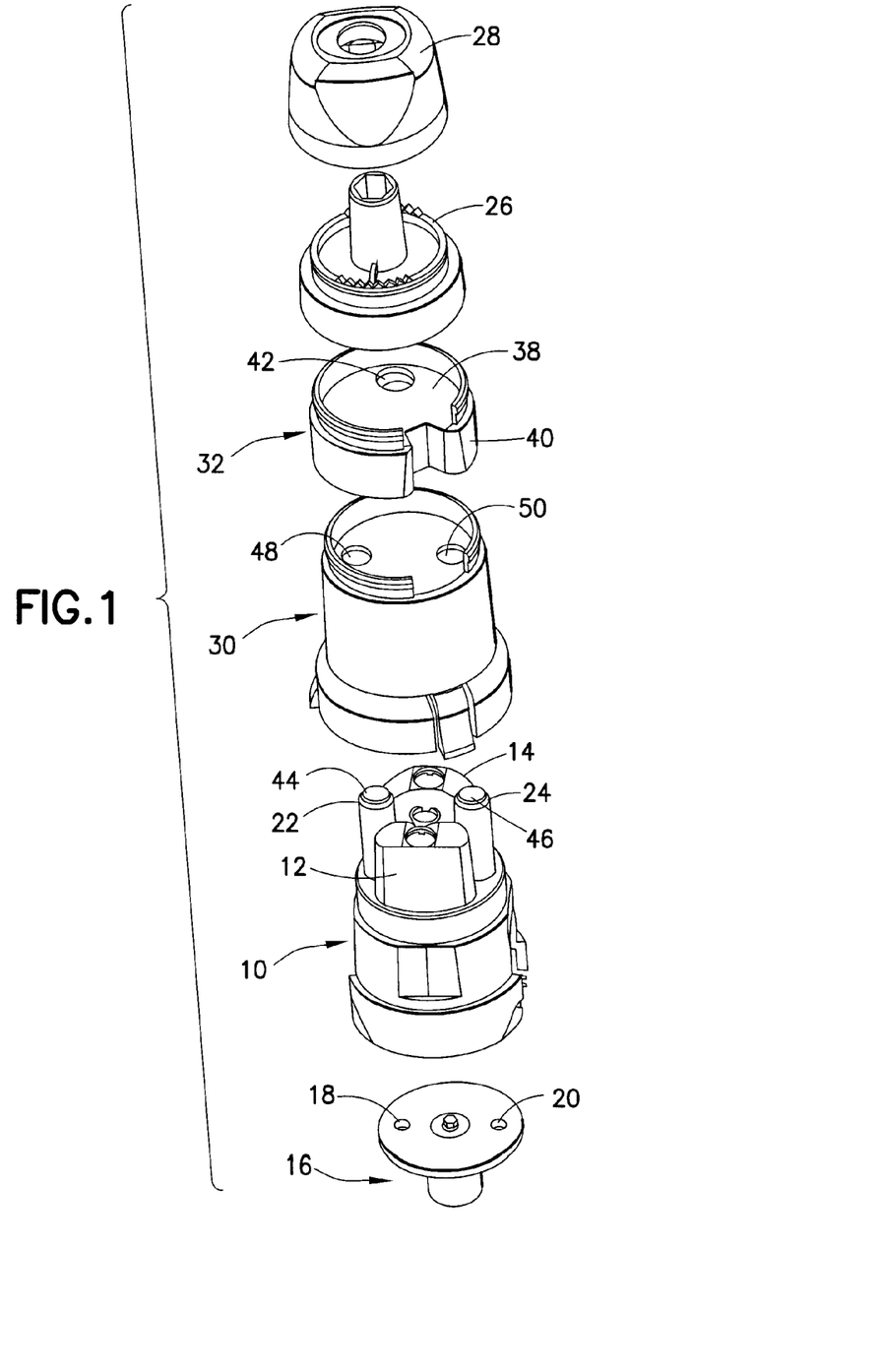
FIGS. 1 and 2 are exploded views of an arrangement of parts, including a polyflux collider arrangement formed in accordance with various embodiments of the present invention, for use with powder dispensers.
Figure 2:
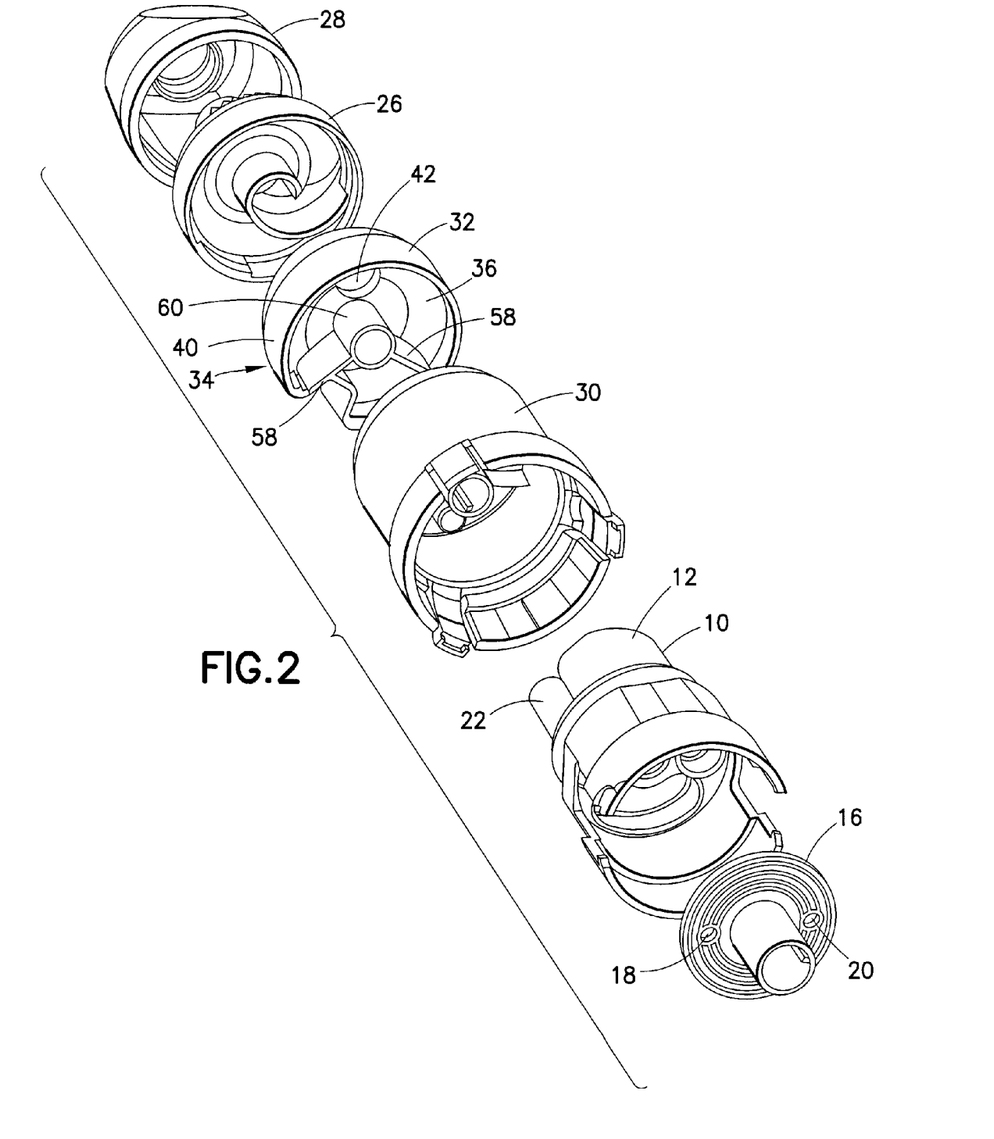

Table 2 shows data for a control test where no polyflux collider arrangement was used. An arrangement of parts as shown in FIGS. 1 and 2 was utilized, but without the polyflux collider. A 400 μg amount of dry powder of mometasone furoate was utilized and tested in the same manner as the tests discussed above with respect to Table 1.

As shown in Table 2, a Fine Particle Fraction (% FPF) of approximately 34.2%-35.6% was achieved. Also, a Fine Particle Dose (FPD) of approximately 124-147 mcg of dry powder (out of 400 μg) was achieved.

TABLE 2

400 μg with no Polyflux Collider Arrangement

|  | Dose 1 | Dose 2 | Dose 3 | Average | Standard Deviation |
|---|---|---|---|---|---|
| Total Recovery | 414.57755 | 373.09539 | 362.75970 | 383.47755 | 27.42 |
| % Recovery | 103.64439 | 93.27385 | 90.68993 | 95.86939 | 6.86 |
| % FPF | 35.69688 | 34.14685 | 34.29108 | 34.71161 | 0.86 |
| FPD | 147.99125 | 127.40033 | 124.39423 | 133.26194 | 12.84 |

In comparing the test results, it can be seen that the polyflux collider arrangement provides a higher amount of a fine particle dose. In particular, a greater percentage of the overall dosage emitted from a DPI has a higher fine particle dose (FPD). Fine particle dose and fine particle fraction are indicators of how many fine particles (in this example, fine particle dose is defined as the amount of particles with a size of less than or equal to 6.5 microns) may be delivered to a determined area in the lungs. This provides an indication of efficacy of delivery of dose. For example, in comparing the results of Table 1 and Table 2, a substantial improvement is seen utilizing a polyflux collider arrangement as opposed to not using (cf., 58.4% FPF average versus 34.7% FPF average; and cf. 217.95916 FPD average versus 133.26194 FPD average). Accordingly, a more effective dose administration can be achieved with various embodiments of the present invention.

Certain aspects of the invention are further described in the following examples. The descriptions of the embodiments of the invention have been presented for purpose of illustration and description. They are not intended to be exhaustive or to limit the invention to the precise forms disclosed, and obviously many modifications and variations are possible in light of the above teaching. The term 'comprising' is defined as 'including but not limited to'.

Percentages are expressed on a weight basis, unless the context clearly indicates otherwise. The mention of any specific drug substance in this specification or in the claims is intended to encompass not only the base drug, but also pharmaceutically acceptable salts, esters, hydrates and other forms of the drug. Where a particular salt or other form of a drug is mentioned, it is contemplated that other salts or forms can be substituted.

What is claimed is:

1. A polyflux collider arrangement for de-agglomerating dry powder in a powder dispenser during inhalation of a dose of dry powder, said polyflux collider arrangement comprising:

spaced-apart first and second inlet openings, a reference plane passing through the centers of said first and second inlet openings; and, a polyflux collider having a body at least partially encompassing a volume and a single exit opening, wherein said first and second inlet openings and said exit opening being in communication with an encompassed volume, said exit opening being spaced from said reference plane;

wherein, the center of said exit opening having a reference axis passing therethrough, said reference axis being perpendicular to said reference plane, said reference axis being spaced and offset from the centers of said first and second inlet openings, and wherein, upon inhalation of a dose, negative pressure is applied to said exit opening which causes a first stream of dry powder to be entrained from said first inlet opening into said encompassed volume and directed towards said exit opening, said negative pressure also causing a second stream of dry powder to be entrained from said second inlet opening into said encompassed volume and directed towards said exit opening, said first and second streams of dry powder colliding in said encompassed volume to form a collective stream passing through said exit opening, said collective stream defining the dose of dry powder.

2. An arrangement as in claim 1, wherein, said first and second inlet openings are formed separately from said body of said polyflux collider.

3. An arrangement as in claim 1 further comprising a swirl nozzle, said collective stream entering said swirl nozzle with discharge from said exit opening.

4. An arrangement as in claim 1, wherein said first and second streams of dry powder are directed towards said exit opening from different directions.

5. An arrangement as in claim 1, wherein said exit opening has an area at least equal to the area of said first inlet opening.

6. A dry powder inhaler comprising the polyflux collider arrangement of claim 1.

7. A drug product comprising the polyflux collider arrangement of claim 1 and at least one active pharmaceutical agent.

8. A drug product comprising the polyflux collider arrangement of claim 1 at least one agglomerate comprising at least one active pharmaceutical agent.

9. The drug product of claim 7, wherein when the dry powder inhaler is actuated, a fine particle fraction of at least about 50% is obtained.

* * * * *